US012788758B2

(12) United States Patent
Radu et al.

(10) Patent No.: US 12,788,758 B2
(45) Date of Patent: Nov. 10, 2026

(54) COMPOSITIONS AND METHODS FOR TREATING CANCER WITH NUCLEOSIDE-METABOLISM MODULATORS

(71) Applicant: The Regents of the University of California, Oakland, CA (US)

(72) Inventors: Caius Gabriel Radu, Los Angeles, CA (US); Evan Robert Abt, Santa Monica, CA (US); Thuc Minh Le, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 742 days.

(21) Appl. No.: 17/631,299

(22) PCT Filed: Jul. 31, 2020

(86) PCT No.: PCT/US2020/044391
§ 371 (c)(1),
(2) Date: Jan. 28, 2022

(87) PCT Pub. No.: WO2021/022105
PCT Pub. Date: Feb. 4, 2021

(65) Prior Publication Data

US 2022/0211710 A1 Jul. 7, 2022

Related U.S. Application Data

(60) Provisional application No. 62/881,058, filed on Jul. 31, 2019.

(51) Int. Cl.

| | |
|---|---|
| ***A61K 31/7048*** | (2006.01) |
| ***A61K 31/519*** | (2006.01) |
| ***A61K 31/708*** | (2006.01) |
| ***A61K 45/06*** | (2006.01) |
| ***A61P 25/02*** | (2006.01) |
| ***G01N 33/50*** | (2006.01) |

(52) U.S. Cl.
CPC .......... *A61K 31/519* (2013.01); *A61K 31/708* (2013.01); *A61K 45/06* (2013.01); *A61P 25/02* (2018.01); *G01N 33/5011* (2013.01)

(58) Field of Classification Search
CPC .... A61K 31/519; A61K 31/708; A61K 45/06; A61P 25/02; G01N 33/5011
See application file for complete search history.

(56) References Cited

U.S. PATENT DOCUMENTS

2018/0313843 A1 11/2018 Keppler et al.

FOREIGN PATENT DOCUMENTS

| | | | | |
|---|---|---|---|---|
| EP | 3163302 | * | 5/2017 | ........... G01N 33/574 |
| EP | 3163302 A1 | * | 5/2017 | ............. A61K 35/76 |
| WO | WO-2020/104762 A1 | | 5/2020 | |
| WO | WO-2021/022105 A1 | | 2/2021 | |

OTHER PUBLICATIONS

Pusztai. Lancet, 2019, 393, 1440-1452. (Year: 2019).*
Serdjebi. Expert Opinion on Drug Metabolism & Toxicology. 2015, 11, 5, 665-672. (Year: 2015).*
Sher. Blood, 2010, 116, 21, 1392. (Year: 2010).*
Jordheim, Nature Reviews Drug Discovery, 12, 2013, 447-464. (Year: 2013).*
Davenne. Characterisation of SAMHD1âs Ancestral Function, University of Oxford, PHD thesis, published Sep. 2018 (Year: 2018).*
Maruyama. Annals of Hematology, 98:131-142 (Year: 2019).*
Pusztai. Lancet, 2019, 393, pp. 1440-1452. (Year: 2019).*
Decherchi et al. Nature Comm. 6:6155. (Year: 2014).*
Tsesmetzis et al. Cancers 2018, 10, 240. (Year: 2018).*
Abt et al.,“ Defective Nucleotide Catabolismefines a Subset of Cancers Sensitive to Purine Nucleoside Phosphorylase Inhibition,” bioRxiv, 810093 (35 pages) (2019).
Balakrishnan et al., “Preclinical and Clinical Evaluation of Forodesine in Pediatric and Adult B-Cell Acute Lymphoblastic Leukemia,” Clinical Lymphoma Myeloma and Leukemia, 13(4): 458-466 (2013).
Gandhi et al., “A proof-of-principle pharmacokinetic, pharmacodynamic, and clinical study with purine nucleoside phosphorylase inhibitor immucillin-H (BCX-1777, forodesine),” Blood, 106(13): 4253-4260 (2005).
International Search Report and Written Opinion for International Application No. PCT/US2020/044391 mailed Nov. 17, 2020.
Ye et al., “Cytidine Deaminase Axis Modulated by miR-484 Differentially Regulates Cell Proliferation and Chemoresistance in Breast Cancer,” Cancer Research, 75(7): 1504-1515 (2015).
Maiti et al., “Structure of the catalytically active APOBEC3G bound to a DNA oligonucleotide inhibitor reveals tetrahedral geometry of the transition state.” Nature Communications 13 (2022): 7117.
Schneider et al., “SAMHD1 is a biomarker for cytarabine response and a therapeutic target in acute myeloid leukemia.” Nature Medicine 23(2) (2017): 250-255.

* cited by examiner

*Primary Examiner* — Scarlett Y Goon
*Assistant Examiner* — Samantha Lynn Schachermeyer
(74) *Attorney, Agent, or Firm* — Foley Hoag LLP; David P. J. Halstead D.; Alexander J. J. Chatterley D.

(57) ABSTRACT

The present invention relates to methods of selecting a subject with cancer for treatment, screening a test molecule for use as a cancer therapeutic, and treating a subject with cancer, as well as compositions for treating cancer.

9 Claims, 10 Drawing Sheets

Forodesine (BCX-1777)

- Target: purine nucleoside phosphorylase
- Approved indications: PTCL (Japan)

COMPOSITIONS AND METHODS FOR TREATING CANCER WITH NUCLEOSIDE-METABOLISM MODULATORS

RELATED APPLICATIONS

This application is a U.S. national stage filing under 35 U.S.C. § 371 of PCT Application No. PCT/US20/44391, filed on Jul. 31, 2020, which claims a right of priority to and the benefit of the filing date of U.S. Provisional Application No. 62/881,058, filed on Jul. 31, 2019, which is hereby incorporated by reference in its entirety.

STATEMENT OF RIGHTS

This invention was made with government support under CA187678, awarded by The National Institutes of Health. The government has certain rights in the invention.

BACKGROUND

In addition to unabated proliferation, alteration of cellular metabolism is a hallmark of cancer. To sustain growth and proliferation, cancer cells must produce sufficient and balanced pools of deoxyribonucleotide triphosphates (dNTPs) for DNA replication and repair. Several drugs targeting dNTP biosynthesis have been explored for cancer treatment but are generally ineffective when administered alone. One such class of drugs is purine nucleoside phosphorylase (PNP) inhibitors, a class that includes forodesine and ulodesine.

Accordingly, there is a need in the field to advance the understanding of fundamental biological processes that determine effectiveness or lack thereof of cancer drugs, and to leverage this knowledge towards the development of new diagnostic and therapeutic approaches that will improve patient care.

SUMMARY OF THE INVENTION

In some aspects, the present disclosure provides methods of selecting a subject with cancer for treatment, screening a test molecule for use as a cancer therapeutic, and treating a subject with cancer, as well as compositions for treating cancer. These aspects are based on the discovery that the test level for a nucleoside-metabolism biomarker relative to a control level can inform the selection and screening methods, as well as allow the treatment methods to be made effective.

In some aspects, methods of selecting a subject with cancer for treatment with an inhibitor of purine nucleoside phosphorylase include determining a test level for a nucleoside-metabolism biomarker in a sample from the subject; and selecting the subject for treatment if the test level passes a control level. In some embodiments, the nucleoside-metabolism biomarker is deoxynucleoside triphosphate triphosphohydrolase SAMHD1, deoxycytidine kinase, cytidine deaminase, or a combination thereof. In some embodiments, the control level is representative of a control subject or control sample that is responsive to treatment with an inhibitor of purine nucleoside phosphorylase. In certain embodiments, the test level for deoxynucleoside triphosphate triphosphohydrolase SAMHD1 passes a control level if it is at most twice as high as the control level. In certain embodiments, the test level for deoxycytidine kinase passes a control level if it is at least half as high as the control level. In certain embodiments, the test level for cytidine deaminase passes a control level if it is at least half as high as the control level. In some embodiments, the test level is determined via immunoblot analysis, RNAseq analysis, DNA sequencing, qPCR, HPLC, mass spectrometry, or a combination thereof.

In some aspects, methods of screening a test molecule for use as a cancer therapeutic include applying the test molecule by contacting it with a test sample or by administering it to a non-human test subject; and determining a test level for a nucleoside-metabolism biomarker from the test sample or from the test subject. In some embodiments, the nucleoside-metabolism biomarker is deoxynucleoside triphosphate triphosphohydrolase SAMHD1, purine nucleoside phosphorylase, deoxycytidine kinase, cytidine deaminase, or a combination thereof.

In certain aspects, methods of treating a subject with cancer include selecting a subject identified as having a test level for a nucleoside-metabolism biomarker that passes a control level (e.g., according to any of the aspects/embodiments disclosed for selecting a subject); and administering to the subject a nucleoside-metabolism modulator. In some embodiments, the nucleoside-metabolism biomarker is deoxynucleoside triphosphate triphosphohydrolase SAMHD1, purine nucleoside phosphorylase, deoxycytidine kinase, cytidine deaminase, or a combination thereof. In certain embodiments, the nucleoside-metabolism modulator is an inhibitor of purine nucleoside phosphorylase (e.g., forodesine or ulodesine). In certain embodiments, the nucleoside-metabolism modulator is an inhibitor of deoxynucleoside triphosphate triphosphohydrolase SAMHD1. In certain embodiments, the nucleoside-metabolism modulator is a vector that effects expression of cytidine deaminase. In certain embodiments, the control level is determined from a control subject or control sample that is responsive to treatment with an inhibitor of purine nucleoside phosphorylase. In certain embodiments, the methods further include determining a test level for a nucleoside-metabolism biomarker after administering to the subject a nucleoside-metabolism modulator; and administering an additional dose of the nucleoside-metabolism modulator if the test level passes a control level. In some embodiments, the methods further include determining a test level for a nucleoside-metabolism biomarker after administering to the subject a nucleoside-metabolism modulator; and administering a higher dose or dosage of the nucleoside-metabolism modulator if the test level fails to pass a control level.

In certain aspects, methods of treating a subject with cancer include administering to the subject a nucleoside-metabolism modulator. In certain embodiments, the nucleoside-metabolism modulator is an inhibitor of purine nucleoside phosphorylase (e.g., forodesine or ulodesine). In certain embodiments, the nucleoside-metabolism modulator is an inhibitor of deoxynucleoside triphosphate triphosphohydrolase SAMHD1. In certain embodiments, the nucleoside-metabolism modulator is a vector that effects expression of cytidine deaminase. In certain embodiments, the control level is determined from a control subject or control sample that is responsive to treatment with an inhibitor of purine nucleoside phosphorylase. In certain embodiments, the methods further include determining a test level for a nucleoside-metabolism biomarker after administering to the subject a nucleoside-metabolism modulator; and administering an additional dose of the nucleoside-metabolism modulator if the test level passes a control level. In some embodiments, the methods further include determining a test level for a nucleoside-metabolism biomarker after administering to the subject a nucleoside-metabolism modulator; and administering a higher dose or dosage of the nucleoside-metabolism modulator if the test level fails to pass a control level.

In certain aspects, disclosed is a nucleoside-metabolism modulator for use in the treatment of a subject with cancer, in which the subject has been identified as having a test level for a nucleoside-metabolism biomarker that passes a control level (e.g., according to any of the aspects/embodiments disclosed for selecting a subject). In some embodiments, the nucleoside-metabolism biomarker is deoxynucleoside triphosphate triphosphohydrolase SAMHD1, purine nucleoside phosphorylase, deoxycytidine kinase, cytidine deaminase, or a combination thereof. In certain embodiments, the nucleoside-metabolism modulator is an inhibitor of purine nucleoside phosphorylase (e.g., forodesine or ulodesine). In certain embodiments, the nucleoside-metabolism modulator is an inhibitor of deoxynucleoside triphosphate triphosphohydrolase SAMHD1. In certain embodiments, the nucleoside-metabolism modulator is a vector that effects expression of cytidine deaminase. In certain embodiments, the control level is determined from a control subject or control sample that is responsive to treatment with an inhibitor of purine nucleoside phosphorylase. In certain embodiments, one may also determine a test level for a nucleoside-metabolism biomarker after administering to the subject a nucleoside-metabolism modulator; and then administer an additional dose of the nucleoside-metabolism modulator if the test level passes a control level. In some embodiments, one may also determine a test level for a nucleoside-metabolism biomarker after administering to the subject a nucleoside-metabolism modulator; and then administer a higher dose or dosage of the nucleoside-metabolism modulator if the test level fails to pass a control level.

In certain aspects, disclosed is a nucleoside-metabolism modulator for use in the treatment of a subject with cancer. In certain embodiments, the nucleoside-metabolism modulator is an inhibitor of purine nucleoside phosphorylase (e.g., forodesine or ulodesine). In certain embodiments, the nucleoside-metabolism modulator is an inhibitor of deoxynucleoside triphosphate triphosphohydrolase SAMHD1. In certain embodiments, the nucleoside-metabolism modulator is a vector that effects expression of cytidine deaminase. In certain embodiments, the control level is determined from a control subject or control sample that is responsive to treatment with an inhibitor of purine nucleoside phosphorylase. In certain embodiments, one may also determine a test level for a nucleoside-metabolism biomarker after administering to the subject a nucleoside-metabolism modulator; and then administer an additional dose of the nucleoside-metabolism modulator if the test level passes a control level. In some embodiments, one may also determine a test level for a nucleoside-metabolism biomarker after administering to the subject a nucleoside-metabolism modulator; and then administer a higher dose or dosage of the nucleoside-metabolism modulator if the test level fails to pass a control level.

In some embodiments, applicable to any of the aspects disclosed herein, the cancer is a leukemia, a lymphoma, a melanoma, or an adenocarcinoma.

In some aspects, compositions include at least two of the following five nucleoside-metabolism modulators: an inhibitor of purine nucleoside phosphorylase, an inhibitor of deoxynucleoside triphosphate triphosphohydrolase SAMHD1, a vector that effects expression of cytidine deaminase, a vector that effects expression of deoxycytidine kinase, and deoxyguanosine.

DETAILED DESCRIPTION OF THE INVENTION

Figure 1:
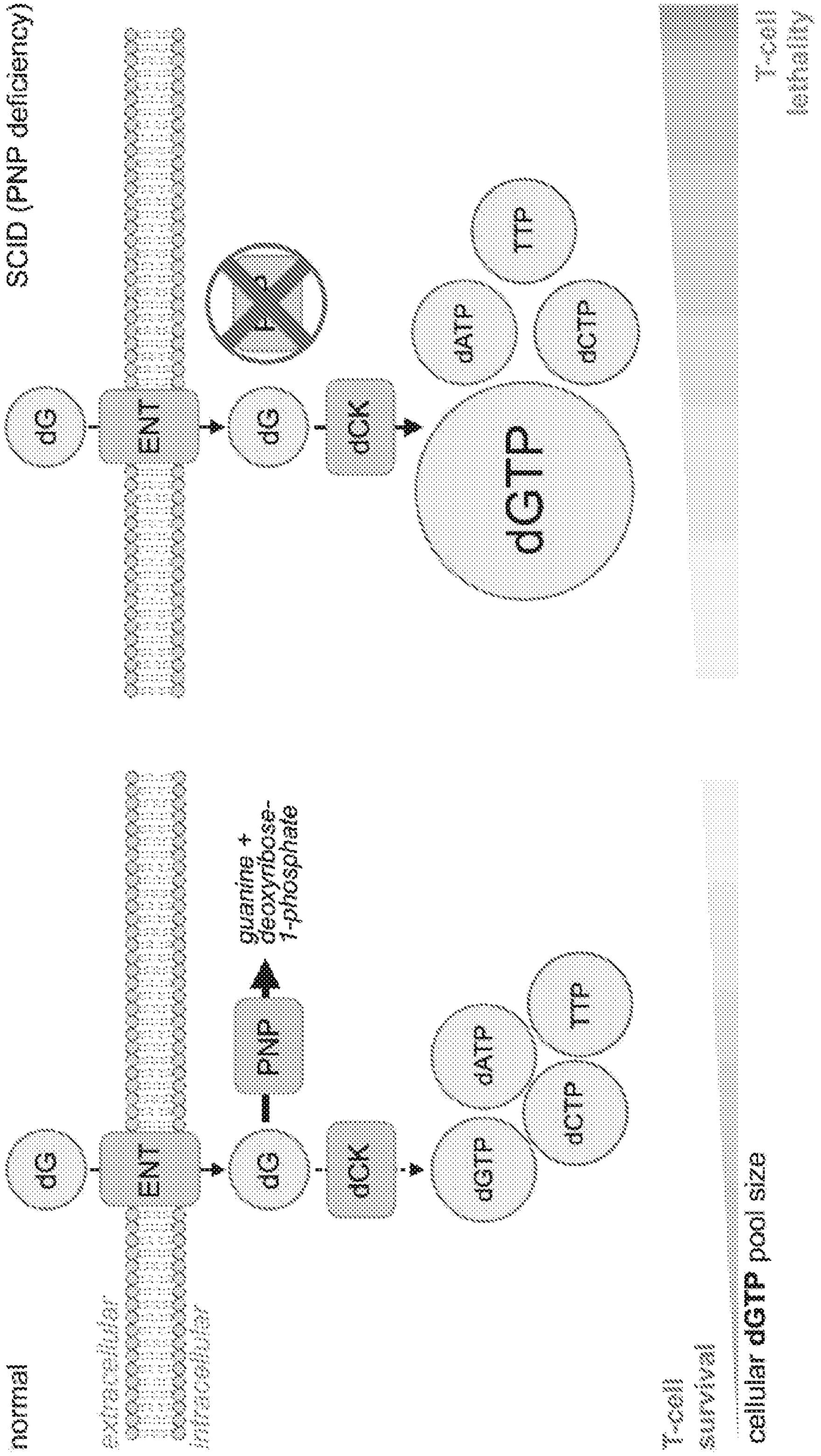
FIG. 1: A schematic depicting that impaired PNP activity results in toxic dGTP accumulation in T-cells.

In some aspects, the present disclosure provides methods of selecting a subject with cancer for treatment, screening a test molecule for use as a cancer therapeutic, and treating a subject with cancer, as well as compositions for treating cancer. These aspects are based on the discovery that the test level for a nucleoside-metabolism biomarker relative to a control level can inform the selection and screening methods, as well as allow the treatment methods to be made effective.

In certain preferred embodiments, the nucleoside-metabolism biomarker is deoxynucleoside triphosphate triphosphohydrolase SAMHD1, deoxycytidine kinase, cytidine deaminase, or a combination thereof, and the cancer treatment is with an inhibitor of purine nucleoside phosphorylase, such as forodesine or ulodesine. In particularly preferred embodiments, the nucleoside-metabolism biomarker is SAMHD1 and the cancer treatment includes the use of an inhibitor of purine nucleoside phosphorylase.

In arriving at the underlying discoveries, a panel of human cancer cell lines was screened for sensitivity to PNP inhibition, using cell viability and proliferation analyses, and enrichment of T-ALL cells was found among the most sensitive models. dCK-mediated nucleoside scavenging was active in all cells tested; however, by applying a LC-MS/MS metabolic assay, it was found that only responding cell lines accumulated dGTP following PNP inhibition. This finding suggested that a defect in dNTP catabolism could be a defining characteristic of cell lines sensitive to PNPi. By performing a transcriptomic analysis, it was determined that only sensitive cell lines were deficient for SAM histidine aspartate containing protein 1 (SAMHD1, also referred in a more expanded terminology as deoxynucleoside triphosphate triphosphohydrolase SAMHD1). SAMHD1 is a non-redundant dNTP triphosphohydrolase that catalyzes the conversion of dNTPs to nucleosides and triphosphate. SAMHD1 protein expression was undetectable in sensitive models. The role of SAMHD1 in mediating resistance to PNP inhibition was confirmed by over expressing SAMHD1 in responding cell lines using retroviral transduction; genetic rescue of SAMHD1 conferred resistance to PNP inhibition.

PNP inhibitors have not previously demonstrated efficacy against solid tumors. However, as disclosed herein, several solid tumor cell line models have been identified as deficient for SAMHD1, including non-small cell lung cancer and melanoma. Using cell viability and proliferation analyses, it was discovered that pharmacological PNP inhibition was highly effective in these models. The role of SAMHD1 was verified by generating CRISPR/Cas9 SAMHD1 knockout pancreatic cancer cells; PNP inhibitors were selectively lethal towards SAMHD1 knockout isogenic pancreatic cancer cells.

SAMHD1 and dCK expression are biomarkers that can be used to stratify patients for response to PNP inhibitors. This work demonstrates that PNP inhibitors (including forodesine and ulodesine) may have utility in treating both hematological cancers and solid tumors characterized by low expression of SAMHD1.

Definitions

As used in the description, the words "a" and "an" can mean one or more than one. As used in the claims in conjunction with the word "comprising," the words "a" and "an" can mean one or more than one. As used in the description, "another" can mean at least a second or more.

The term "treating" includes curing, relieving, or ameliorating to any extent a symptom of an illness or medical condition or preventing further worsening of such a symptom. For example, treating cancer includes making the cancer less severe.

A "biomarker" can be anything that can be used as an indicator of a particular physiological state of an organism. For example, a biomarker can be a level of a metabolite, by-product, mRNA, enzyme, peptide, polypeptide, or protein associated with a particular physiological state. When referring to a biomarker in this specification, no effective distinction is made between a peptide and a polypeptide.

A "nucleoside-metabolism biomarker" can be any biomarker that has a role in biological reactions that involve nucleosides. For example, any enzyme that converts (e.g., via a catabolic reaction) or creates (e.g., via a synthesis reaction) a nucleoside (e.g., deoxyadenosine, deoxyguanosine, thymidine, deoxyuridine, deoxycytidine, adenosine, guanosine, uridine, cytidine) is a nucleoside-metabolism biomarker. In some embodiments, nucleoside-metabolism biomarkers also include non-enzyme participants of the nucleoside reactions. For example, a nucleoside-metabolism biomarker includes any enzyme that converts or creates deoxyguanosine as well as the associated metabolites ("deoxyguanosine-metabolism biomarker," which can be a "deoxyguanosine-metabolism enzyme" or a "deoxyguanosine-metabolism metabolite").

The term "nucleoside-metabolism modulator" includes any molecule that modulates the activity of a nucleoside-metabolism biomarker. For example, when the nucleoside-metabolism biomarker is an enzyme, the nucleoside-metabolism modulator can be an inhibitor of that enzyme. In particular, when deoxynucleoside triphosphate triphosphohydrolase SAMHD1 is the nucleoside-metabolism biomarker, the nucleoside-metabolism modulator can be forodesine or ulodesine.

The term "level," for example when forming a compound noun with a preceding word such as test or control, can denote a measurable value such as an amount, concentration, activity, maximum rate, Michaelis constant, half-maximal effective concentration, or half-maximal inhibitory concentration (e.g., of a biomarker or another tissue ingredient that is related to a biomarker). The term "level" also includes values such as presence or absence, which can be discrete when measured individually or can attain a more continuous character when measured collectively.

The term "passes a control level" means that the measured value, such as a test level, is more than or less than a threshold value, which threshold value differs by more than a certain amount (e.g., 5%, 10%, 15%, 20%, 25%, 30%, 35%, 40%, 45%, 50%, 55%, 60%, 65%, 70%, 75%, 80%, 85%, 90%, 95%, 100%) from another value, such as a control level. As an example, in certain embodiments, the difference is 10% (i.e., resulting in a threshold of 90% of the control level if the test level must be high (i.e., at least 90% of the control level or higher), and resulting in a threshold of 110% of the control level if the test level must be low (i.e., 0 to 110% of the control level)). As used herein, the control level is preferably a level representative of subjects, cancers, or cell lines sensitive to a therapy, e.g., treatment with a PNP inhibitor. The test level and the control level are presumed to be in a form that positively correlates with the nucleoside-metabolism biomarker (e.g., a higher amount or activity of the nucleoside-metabolism biomarker provides a higher test/control level). The control level can be obtained from one sample, one subject, more than one sample by averaging, more than one subject by averaging, or from otherwise available values (e.g., published articles, accessible databases).

The phrase "pharmaceutically-acceptable carrier" as used herein means a pharmaceutically-acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "subject" refers to a mammal, including, but not limited to, a human or non-human mammal, such as a bovine, equine, canine, ovine, or feline.

Samples and Biomarker Detection

A biological sample can be obtained from an individual for use in the methods disclosed herein. The biological sample can be a biological fluid sample take from a subject. The sample may be obtained from the subject using a variety of methods that are known in the art.

The methods disclosed herein can include detecting levels of a biomarker, in a subject or a biological sample obtained from the subject, and comparing them to their levels in a reference sample (or to a threshold level that is based on a control level obtained from a reference sample). Detecting alterations in the expression level of a biomarker can include measuring the level of protein or mRNA of the biomarker and comparing it to a control (e.g., directly comparing with a control, indirectly comparing to a control by directly comparing to a threshold based on the control). Additionally, or alternatively, the methods can include genotyping or haplotyping the gene encoding the biomarker in a subject or a biological sample obtained from the subject, and comparing it with a control. In some embodiments, the biological sample is one that is isolated from the subject.

Methods of Selecting a Subject

In some aspects, the disclosure relates to methods of selecting a subject with cancer for treatment with an inhibitor of purine nucleoside phosphorylase. The methods include determining a test level for a nucleoside-metabolism biomarker in a sample from the subject, and selecting the subject for treatment if the test level passes a control level.

In some embodiments, the nucleoside-metabolism biomarker is deoxynucleoside triphosphate triphosphohydrolase SAMHD1, deoxycytidine kinase, cytidine deaminase, or a combination thereof.

In practicing these methods, a test level for a nucleoside-metabolism biomarker would pass a control level if, in some embodiments, it is at most twice as high as the control level for deoxynucleoside triphosphate triphosphohydrolase SAMHD1 (e.g., test level is 20%, 40%, 60%, 80%, 100%, 120%, 140%, 160%, 180%, 200% of the control level, or is at any value between these values), at least half as high as the control level for deoxycytidine kinase (e.g., test level is 50%, 100%, 200%, 400%, 800%, 2000% of the control level, or is at any value between these values), and/or at least half as high as the control level for cytidine deaminase (e.g., test level is 50%, 100%, 200%, 400%, 800%, 2000% of the control level, or is at any value between these values).

Methods of Screening a Test Compound

In some aspects, the disclosure relates to methods of screening a test molecule (e.g., small molecule, biological molecule) for use as a cancer therapeutic. The methods include contacting the test molecule with a test sample, and then determining a test level for a nucleoside-metabolism biomarker from the test sample, or alternatively, administering the test molecule to a non-human subject (e.g., mouse), and then determining a test level for a nucleoside-metabolism biomarker from the test subject.

In various methods, the levels (e.g., test levels) can be determined via immunoblot analysis, RNAseq analysis, DNA sequencing, qPCR, HPLC, mass spectrometry, or a combination thereof.

Methods of Treating a Subject

In some aspects, the disclosure relates to a method of treating a subject who has cancer (e.g., treating a subject, treating a selected subject, further treating a previously treated subject). For treatment, a nucleoside-metabolism modulator can be administered to the subject. The nucleoside-metabolism modulator can be an inhibitor of purine nucleoside phosphorylase (e.g., forodesine or ulodesine). A number of purine nucleoside phosphorylase inhibitors (i.e., PNP inhibitors), including forodesine and ulodesine, are well known in the art (see, e.g., G. A. Kicska et al., Immucillin H, a powerful transition-state analog inhibitor of purine nucleoside phosphorylase, selectively inhibits human T lymphocytes, PNAS 98(8): 4593-98 (2001); J. C. Sircar, Inhibitors of human purine nucleoside phosphorylase. Synthesis, purine nucleoside phosphorylase inhibition, and T-cell cytotoxicity of 2,5-diaminothiazolo[5,4-d]pyrimidin- 7(6H)-one and 2,5-diaminothiazolo[4,5-d]pyrimidin-7(6H)-one. Two thioisosteres of 8-aminoguanine, J. Med. Chem 29(9): 1804-06 (1986); U.S. Pat. No. 6,174,888 (issued Jan. 16, 2001); U.S. Pat. No. 5,721,240 (issued Feb. 24, 1998); U.S. Pat. Appl. Publ'n No. 20020061898 (published May 23, 2002); U.S. Pat. Appl. Publ'n No. 20070027113 (published Feb. 1, 2007), all of which are hereby incorporated by reference in their entireties, and particularly for their disclosure of PNP inhibitors). These and any other suitable PNP inhibitors can be used in the disclosed treatment methods.

Additional PNP inhibitors have been disclosed in various publications (e.g., Evans et al. in Organic Letters (2003) 5:3639; Taylor et al. in Journal of American Chemical Society (2007) 129:6984; Evans et al. in Journal of Medicinal Chemistry (2003) 46:5271; Castilho et al. in Bioorganic & Medicinal Chemistry (2006) 14:516; Schramm et al. in Journal of Biological Chemistry (2007) 282:28297; and Bantia et al. in International Immunopharmacology (2010) 784 and (2001) 1: 1199-1210; Kicska et al. in Proceedings of National Academy of Sciences (2001) 98:4593-4598). The disclosures of each of these references are hereby incorporated by reference herein in their entirety by this citation, and particularly for their disclosure of PNP inhibitors. Further non-limiting examples of PNP inhibitors include those disclosed in U.S. Pat. Nos. 4,985,433; 4,985,434, 5,008,265; 5,008,270; 5,565,463 7,427,624, 5,721,240, 5,985,848, 7,390,890 and the continuation patents that are referenced therein, U.S. Pat. Nos. 7,109,331, 8,283,345, 8,173,662 and 7,553,839, Int'l Pat. No. WO2008/030119, and EP2395005, the disclosures of which are also incorporated herein in their entirety by this reference, and particularly for their disclosure of PNP inhibitors.

In some embodiments, the nucleoside-metabolism modulator can be an inhibitor of deoxynucleoside triphosphate triphosphohydrolase SAMHD1 or a vector that effects expression of cytidine deaminase.

In methods that include adjusting the treatment dose or dosage, the test level for a nucleoside-metabolism biomarker can be compared to a control level to determine whether to continue the treatment, whether to reduce its dose or dosage, or whether to increase its dose or dosage. The test level that passes a control level need not be the same for different aspects disclosed herein. For example, when selecting a subject for treatment with an inhibitor of purine nucleoside phosphorylase relying on a test level for deoxynucleoside triphosphate triphosphohydrolase SAMHD1, a test level that is at most twice as high as the control level might be chosen, whereas when screening a test molecule for use as a cancer therapeutic relying on the ability of the test molecule to inhibit deoxynucleoside triphosphate triphosphohydrolase SAMHD1, a test level that is much higher (e.g., four times as high) than the control level might be chosen (e.g., if the test sample or test subject used for the screening originally had a high non-responsive level of deoxynucleoside triphosphate triphosphohydrolase SAMHD1, then even if the test molecule does not bring that level down to the level of the control level, as long as it effectively reduces it, the test molecule might be chosen as a candidate for further testing).

Compositions and Formulations

In some aspects, the invention relates to a composition comprising a nucleoside-metabolism modulator. The composition may comprise a pharmaceutically acceptable carrier. The pharmaceutical compositions disclosed herein may be delivered by any suitable route of administration (e.g., oral, intravenous), and can be supplied in various forms (e.g., powders, ointments, drops, liquids, gels, tablets, capsules, pills, or creams).

The selected dosage level, as can be determined by a medical practitioner, will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

EXAMPLE

Defective Nucleotide Catabolism Defines a Subset of Cancers Sensitive to Purine Nucleoside Phosphorylase Inhibition Pharmacological inhibition of purine nucleoside phosphorylase (PNP) has been explored as a treatment strategy for leukemia and lymphoma. However, the determinants of cancer cell sensitivity to PNP inhibition are incompletely understood. PNP inhibitors impair cell proliferation by preventing catabolism of the nucleoside deoxyguanosine (dG) and allowing for its phosphorylation by nucleoside kinases, ultimately resulting in toxic imbalances amongst intracellular deoxyribonucleotide triphosphate (dNTP) pools. We hypothesized that differential nucleoside uptake, or catabolism defines cancer cell lines as either sensitive or resistant to PNP inhibition. Using an integrated analysis of proliferation inhibition and cell cycle-phase distribution, we found that T-cell acute lymphoblastic leukemia (T-ALL) cells are uniquely and acutely sensitive to PNP inhibition. We determined that although the nucleoside scavenging kinase deoxycytidine kinase (dCK) was active in all cells tested, only responding cell lines accumulated dGTP following PNP inhibition. Evaluating the expression of genes involved in nucleoside scavenging, biosynthesis, and phosphohydrolysis across a panel of sensitive and resistant cell lines, we found that the dNTP phosphohydrolase, SAM histidine aspartate containing protein 1 (SAMHD1), was exclusively expressed in resistant models.

Using CRISPR/Cas9 SAMHD1 knockout cell lines, we verified that PNP inhibitor sensitivity is a function of SAMHD1 expression and determined that the pharmacological inhibition of dCK or genetic restoration of SAMHD1 conferred resistance to PNP inhibition in a sensitive T-ALL cell line. Importantly, we determined that a subset of established and primary solid tumors models are SAMHD1-deficient and that these models are acutely sensitive to PNP inhibitors indicating that the utility of PNP inhibitors can be expanded beyond hematological malignancies. Additionally, we found that deoxycytidine can limit the anti-proliferative effects of PNPi but this effect can be overcome by expression of deoxycytidine-catabolizing gene cytidine deaminase (CDA). Collectively, these results indicate that SAMHD1, dCK, and CDA are critical biomarkers that can be used to stratify patients in clinical trials evaluating pharmacological PNP inhibition.

Introduction

A sufficient supply of deoxyribonucleotide triphosphates (dNTPs) is essential for cell growth, survival and proliferation.[1,2] Nucleotide biosynthetic networks are tightly regulated by transcriptional, post-translational, and allosteric feedback mechanisms. The dependence of cancer cells on dNTP production has been leveraged therapeutically by the use of small molecule inhibitors of key biosynthetic enzymes including ribonucleotide reductase, dihydrofolate reductase and thymidylate synthase in the clinic. These drugs restrict the ability of cancer cells to synthesize dNTPs, trigger cell cycle arrest, and prevent cell proliferation. Beyond insufficiency, imbalance among dNTP pools results in altered cell cycle progression and death in certain cell types including T- and B-cells.

Intriguingly, this cell type specific lethality resulting from dNTP imbalance is a cause of the pathology severe-combined immuno-deficiency (SCID), a genetic disorder that results in severely compromised immune function and premature death. Giblett and colleagues were among the first to identify that mutations in the nucleotide catabolic enzymes adenosine deaminase (ADA) and purine nucleoside phosphorylase (PNP) drive the development of SCID.[3] PNP and ADA both function in the catabolism of purine deoxyribonucleosides and counter their intracellular accumulation by deoxycytidine kinase (dCK). PNP inhibition prevents the catabolism of deoxyguanosine (dG), thereby allowing the intracellular conversion of dG to dGTP, which can prevent de novo biosynthesis of pyrimidine dNTPs via allosteric inhibition of ribonucleotide reductase.[4,5] For reasons not well understood, PNP and ADA deficiency results in selective T- and B-cell defects, and otherwise normal cellular development, in individuals diagnosed with SCID (FIG. 1).

The observations made by Giblett and colleagues were eventually leveraged for the treatment of T- and B-cell leukemias and lymphomas with the rationale that pharmacological inhibition of ADA or PNP could be an effective treatment strategy for patients suffering from these malignancies.[6,7] In 1998, Schramm and colleagues spearheaded the effort to develop small molecule PNP inhibitions and utilized their knowledge of the transition state substrate-inhibition structure of PNP to rationally design drugs with exceptionally high potency and selectivity.[8] Pharmacological PNP inhibition was found to selectively eradicate T-cell leukemias in vitro thus mimicking the SCID phenotype.[4] With these encouraging results, the PNP inhibitor Forodesine (also known as BCX-1777 or Immucillin H) progressed to clinical trials for the treatment of relapsed/refectory T- and B-cell leukemias and lymphomas and received approval for the treatment of peripheral T-cell lymphoma in Japan in 2017.[9,10] Despite excellent tolerability and pharmacodynamic properties in humans (evidenced by accumulation of the PNP substrate dG in plasma), only a subset of patients responded to treatment.

It remains an open challenge to identify biomarker predictive of PNP inhibitor response in cancer. Multiple markers such as ATM, p53, ZAP-70, equilibrate nucleoside transporters (ENT) and HGPRT have been studied in this context but alone do not predict sensitivity.[11] [12] With the goal of identifying metabolic determinants of PNP inhibitor response, we focused our investigation on heterogeneity in nucleoside uptake, accumulation and catabolism across panels of cancer cell lines. We found that the dNTP phosphohydrolase SAM histidine aspartate containing protein 1 (SAMHD1), which catabolizes dGTP into dG and triphosphate, was expressed exclusively in resistant cell lines. We confirmed a role for SAMHD1 in the activity of PNP inhibitors using both loss of function and gain of function genetic models. Additionally, we identified several solid tumor cell lines, including lung cancer and melanoma, which do not express SAMHD1. We confirmed that these models were sensitive to PNP inhibition, demonstrating that SAMHD1 expression and disease type per se is a determinant for PNP inhibitor sensitivity.

Materials and Methods: Experimental Model and Subject Details

Cell Culture

All cell cultures were between passages 3 and 20 and maintained in antibiotic free DMEM or RPMI+10% dialyzed FBS, at 37° C. in 5% $CO_2$. We routinely monitored for *mycoplasma* contamination using the PCR-based Venor Mycoplasma kit. PDAC cell lines were acquired either from a commercial vendor (ATCC, DSMZ) or from collaborators. Cell line identity was independently authenticated by PCR.

Drugs

Drug stocks were prepared in DMSO or $H_2O$ and diluted fresh in cell culture media for treatments.

Propidium Iodide Cell Cycle Analysis

Treated cells were washed with PBS and suspended in propidium iodide cell cycle staining solution (100 μg/ml propidium iodide; 20 μg/ml Ribonuclease A). 10,000 events were collected per sample. All flow cytometry data were acquired on five-laser BD LSRII, and analyzed using FlowJo software (Tree Star).

Viability Analysis

For CellTiter-Glo analysis cells were plated at $1\times10^3$ cells/well in 50 μl/well in white opaque 384-well plates and treated as described. Following incubation 50 μl of CellTiter-Glo reagent (Diluted 1:5 in $dH_2O$) was added to each well, plates incubated at room temperature for 5 m and luminescence was measured using a BioTek microplate luminescence reader. Proliferation rate normalized growth inhibition was calculated using the previously described GR metric (Hafner et al., 2016).

For crystal violet staining, cells were plated in 6-well cell culture plates at $1\times10^4$ cells/well and treated as described. Following treatment cells were fixed by incubating in 4% PFA in PBS for 15 m at room temperature. Plates were subsequently washed with PBS and stained with 0.1% crystal violet in $H_2O$ for 15 m at room temperature.

Immunoblot Analysis

PBS-washed cell pellets were re-suspended in cold RIPA buffer supplemented with protease and phosphatase inhibitors. Protein lysates were normalized using BCA assay, diluted using RIPA and 4× laemmli loading dye, resolved on 4-12% Bis-Tris gels and electro-transferred to nitrocellulose membranes. After blocking with 5% nonfat milk in TBS+0.1% Tween-20 (TBS-T), membranes were incubated overnight in primary antibodies diluted (per manufacturers instructions) in 5% BSA in TBS-T. Membranes were washed with TBST-T and incubated with HRP-linked secondary antibodies prepared at a 1:2500 dilution in 5% nonfat dry milk in TBS-T. HRP was activated by incubating membranes with a mixture of SuperSignal Pico and SuperSignal Femto ECL reagents (100:1 ratio). Exposure of autoradiography film was used for detection.

Retroviral Transduction and Stable Cell Line Generation

The pMSCV-hCDA-IRES-EYFP plasmid was described previously.[13] Amphotropic retroviruses were generated by transient co-transfection of the MSCV retroviral plasmid and pCL-10A1 packaging plasmid into Phoenix-Ampho packaging cells.

Results

SAMHD1 Mediates Response to PNP Inhibition in Leukemia Cell Lines

Figure 2A:
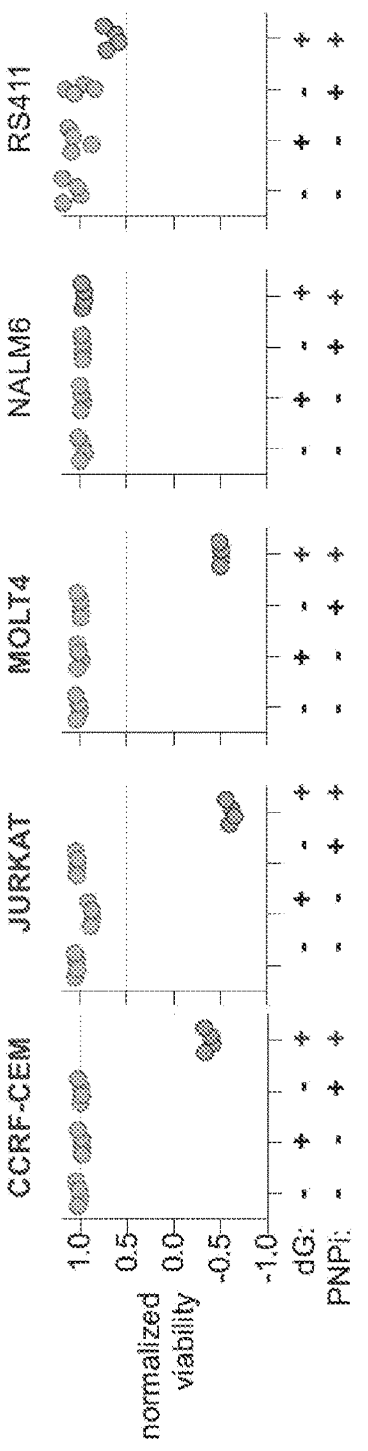
FIGS. 2A to 2L: Experimental results indicating that purine nucleoside phosphorylase (PNP) inhibition is selectively lethal in a subset of acute lymphoblastic leukemia cell lines. (2A) Cell Titer Glo analysis of acute lymphoblastic leukemia cell line panel treated with 5 μM dG±1 μM BCX-1777 for 72 h (PNPi, n=4). (2B) Propidium iodide (PI) cell cycle analysis of acute lymphoblastic leukemia cell lines treated with 5 μM dG±1 μM BCX-1777 for 24 h. Insert indicate percentage of Sub-G1 population. (2C) Immunoblot analysis of NALM6 or CCRF-CEM cells treated with 5 μM dG±1 μM BCX-1777 for 24 h. (2D) Model summarizing metabolic defects potentially explaining sensitivity to PNP inhibitors. (2E) 2D chemical representation of forodesine, a PNP inhibitor that has been developed for the treatment of leukemia and lymphoma, which exhibits limited efficacy. (2F) Expression of dCK, PNP and SAMHD1 across T-ALL cell lines in the Cancer Cell Line Encyclopedia (CCLE) RNAseq dataset. (2G) Immunoblot analysis of dCK and SAMHD1 expression in T- and B-ALL cell lines. (2H) LC-MS/MS analysis of extracellular dG and intracellular dGTP following PNPi±dCKi in JURKAT T-ALL cells. dGTP accumulation in T-ALL requires PNP inhibition and active dCK. (2I) Immunoblot validation of SAMHD1 over-expression in CCRF-CEM T-ALL cells. (2J) dG+PNPi IC-50 in CCRF-CEM-YFP and -SAMHD1 cells. (2K) Cell Titer Glo analysis of CCRF-CEM YFP control and SAMHD1-over-expressing isogenic cells treated with 5 μM dG±1 μM BCX-1777 for 72 h (PNPi, n=4). (2L) PI cell cycle analysis of CCRF-CEM YFP control and SAMHD1-over-expressing isogenic cells treated with 5 μM dG±1 μM BCX-1777 for 24 h. Insert indicate percentage of Sub-G1 population.
Figure 2B:
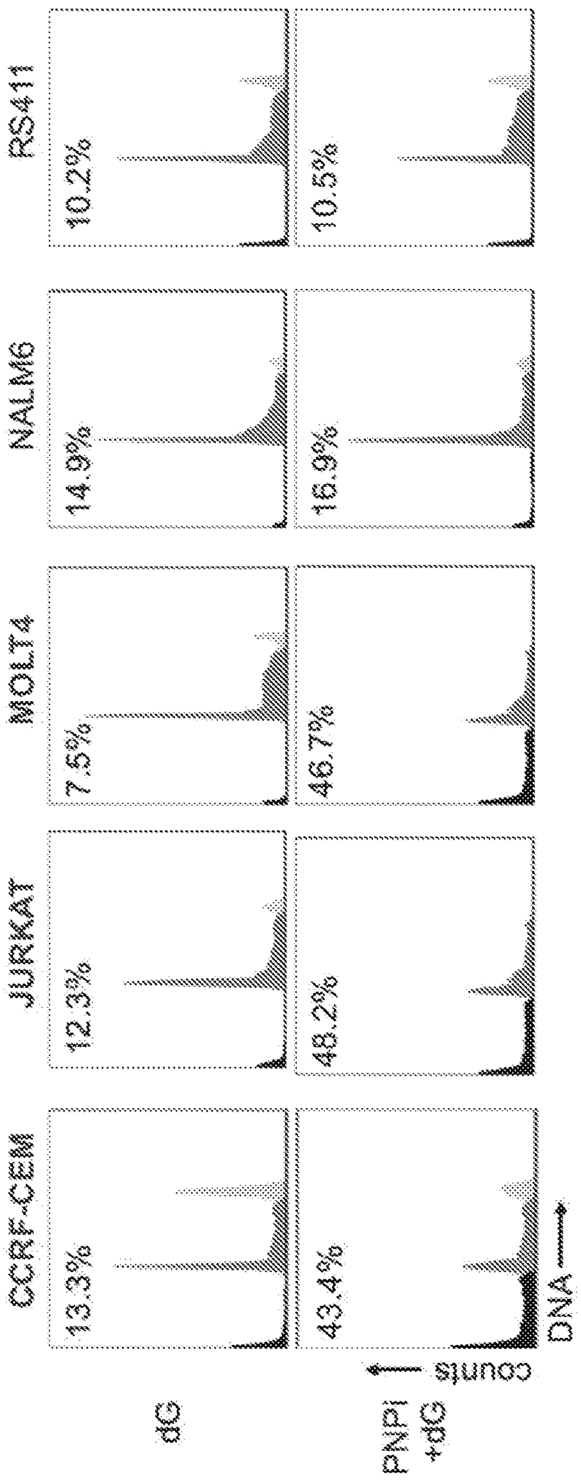
Figure 2C:
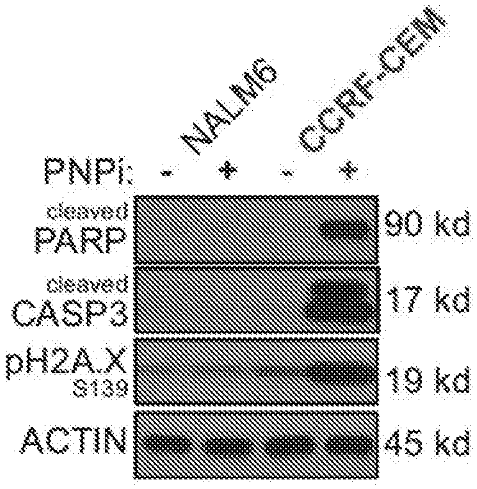

To identify cell line models sensitive and resistant to PNP inhibition, we tested the anti-proliferative effects of dG, Forodesine (PNPi), and the combination across a panel of T- and B-acute lymphoblastic leukemia (ALL) cell line using Cell Titer Glo. We found that the T-ALL cell lines CCRF-CEM, JURKAT and MOLT-4 were eradicated by the combination whereas the B-ALL models were unaffected (FIG. 2A). We confirmed these findings using flow cytometry cell cycle analysis in which we observed an increase in the percentage of sub-G1 cells, a maker for cell death, following PNPi treatment only in T-ALL models (FIG. 2B). Additionally, using immunoblot analysis, we found that PNPi treatment induced DNA damage (evidenced by $H2AX_{S139}$ phosphorylation) and apoptosis (evidenced by cleaved caspase 3 accumulation) in only CCRF-CEM and not in NALM6 cells (FIG. 2C).

Figure 2D:
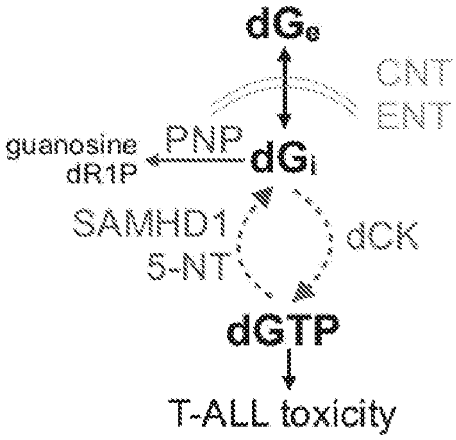
Figure 2E:
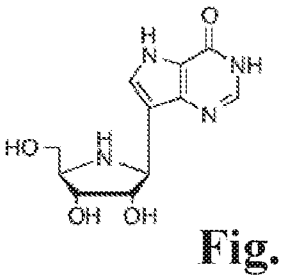
Figure 2F:
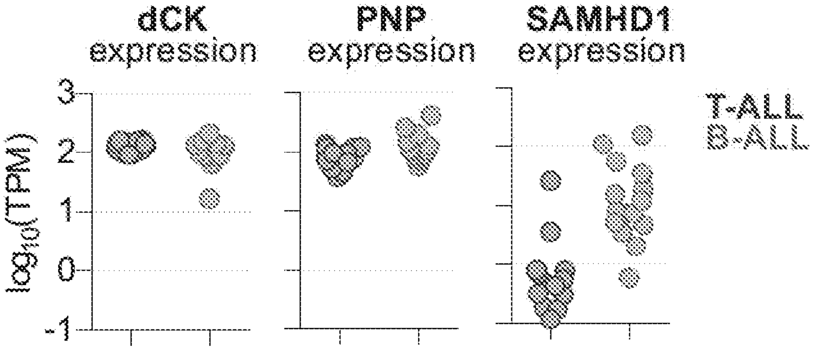
Figure 2G:
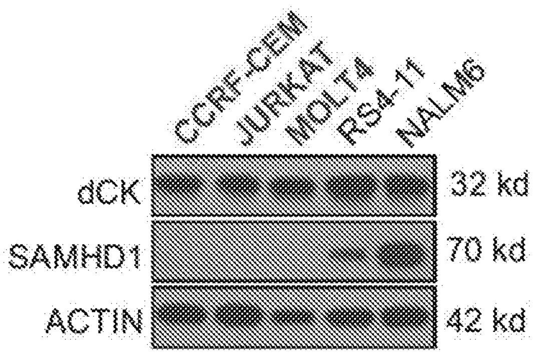
Figure 2H:
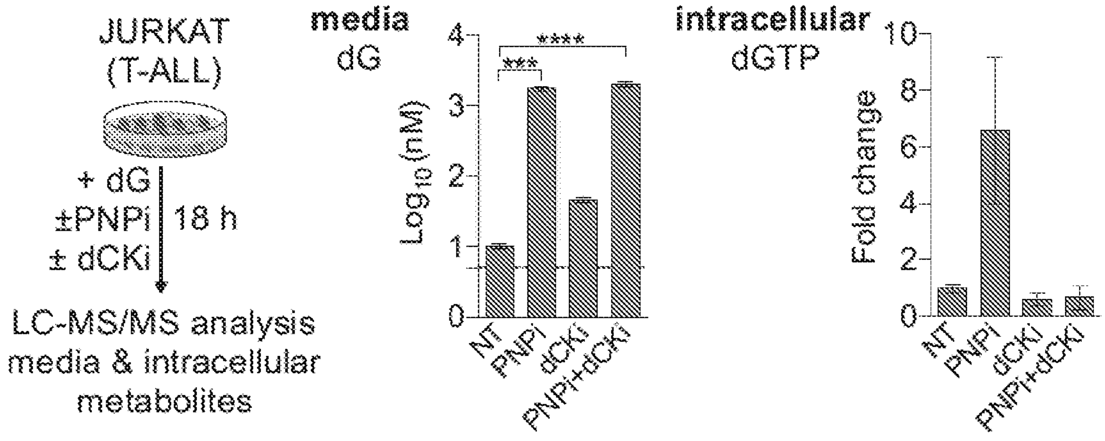
Figure 2I:
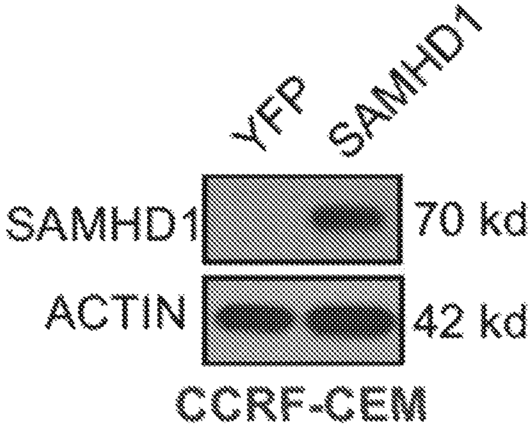
Figure 2K:
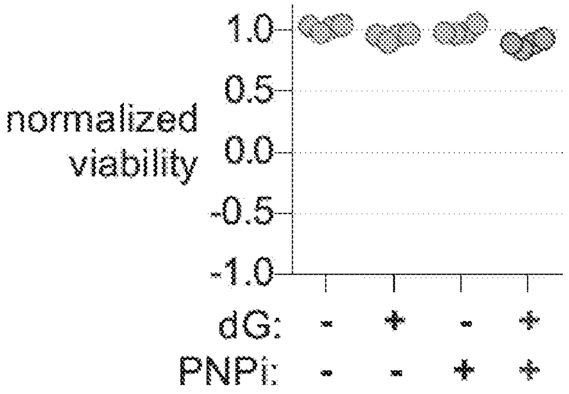
Figure 2J:
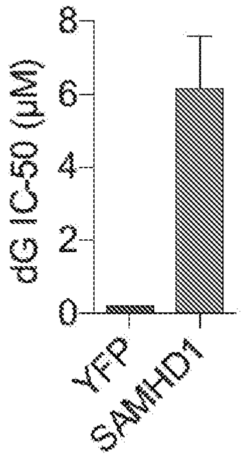
Figure 2L:
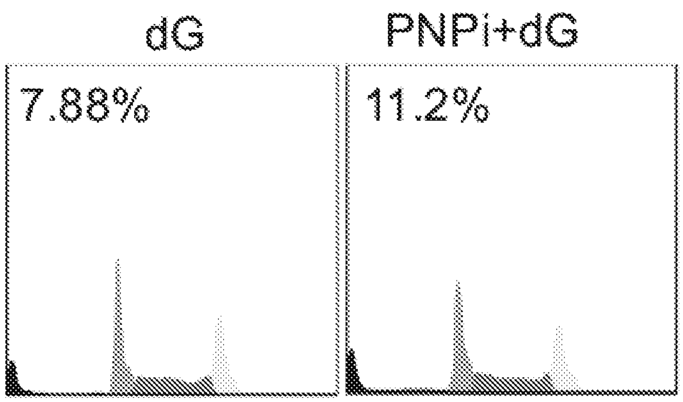

We reasoned that heterogeneity in the sensitivity to PNP inhibition could arise from the differential expression of key metabolic genes essential for the synthesis and accumulation dGTP from dG. These genes include PNP itself, dCK, essential and non-redundant for its ability to phosphorylate dG to dGMP, and SAMHD1, a dNTP phosphohydrolase that catabolizes dGTP to dG (FIG. 2D). By probing the Cancer Cell Line Encyclopedia (CCLE) gene expression database, we found that dCK and PNP were expressed at similar levels across T- and B-ALL cell line models. However, SAMHD1 was found to be expressed at high levels exclusively in B-ALL cell lines and undetectable in a subset of T-ALL cell lines (FIG. 2F). Using immunoblot analysis, we confirmed this gene expression pattern that dCK is expressed at similar levels across T- and B-ALL models but SAMHD1 is only detected in B-ALL cell lines (FIG. 2G). To functionally validate the role of SAMHD1 in the response to PNP inhibition, we engineered a variant a CCRF-CEM cells that constitutively express human SAMHD1 using retroviral transduction (FIG. 2I). We found that expression of SAMHD1 rendered CCRF-CEM cells completely resistant to the anti-proliferative (FIG. 2K) and cytotoxic effects of PNPi (FIG. 2F).

SAMHD1-Deficient Solid Tumor Models are Sensitive to PNP Inhibitors.

Figures 3A, 3B, 3C, 3D, 3E:
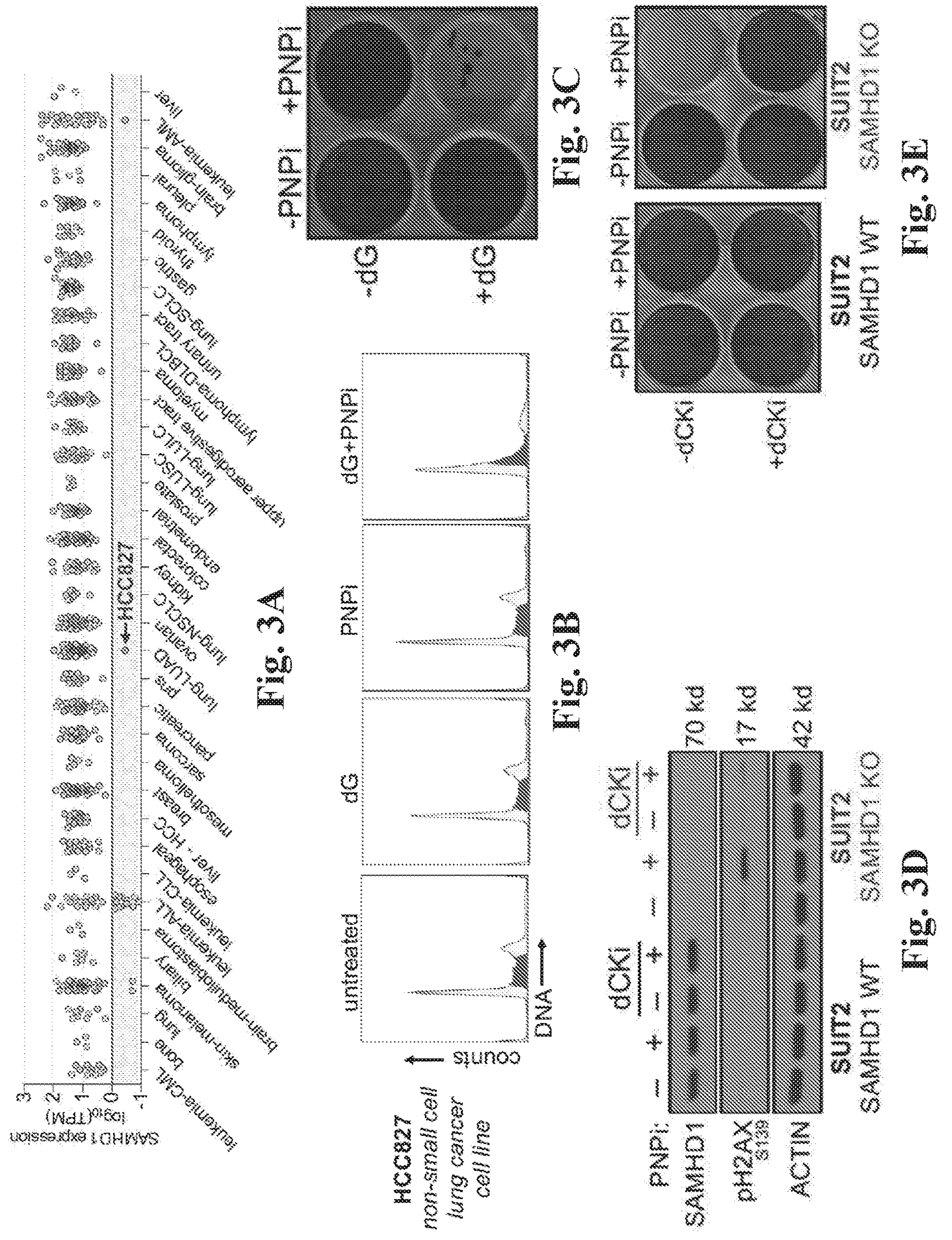
FIGS. 3A to 3E: Experimental results indicating that SAMHD1 protects solid tumor-derived cell lines from PNP inhibition. (3A) SAMHD1 expression in the cancer cell line encyclopedia (CCLE) RNAseq dataset. (3B) PI cell cycle analysis of the HCC827 non-small cell lung cancer cell line treated with 5 μM dG±1 μM BCX-1777 (PNPi) for 24 h. (3C) Crystal violet analysis of HCC827 cells treated for 7 d with 5 μM dG±1 μM PNPi for 7 d. Media was refreshed every 72 h. (3D) Immunoblot analysis of SUIT2 wild-type (WT) and SAMHD1 knockout (KO) cells treated for 24 h+5 μM dG±1 μM forodesine±1 μM (R)-DI-82 (dCKi). (3E) Crystal violet analysis of SUIT2 WT and SAMHD1 KO cells treated for 7 d with 5 μM dG±1 μM PNPi±1 μM dCKi for 7 d. Media was refreshed every 72 h.

To evaluate the spectrum of SAMHD1 expression across cancers and to determine if low SAMHD1 expression was unique to T-ALL, we extended our analysis to the complete CCLE gene expression dataset (FIG. 3A). In addition to ALL models, we identified several cell line models exhibiting low expression of SAMHD1, including melanoma, lung adenocarcinoma, and acute myeloid leukemia cell lines. To determine if low SAMHD1 expression predicts response to PNP inhibitors in solid tumor models, we evaluated the activity of PNPi in the lung adenocarcinoma cell line HCC827. Using flow cytometry, we found that the combination of dG and PNPi induced cell cycle arrest in HCC827 cells (FIG. 3B). We determined that this associated with proliferation inhibition by performing crystal violet analysis of HCC827 cell cultured treated for 7 d (FIG. 3C).

Figure 4A:
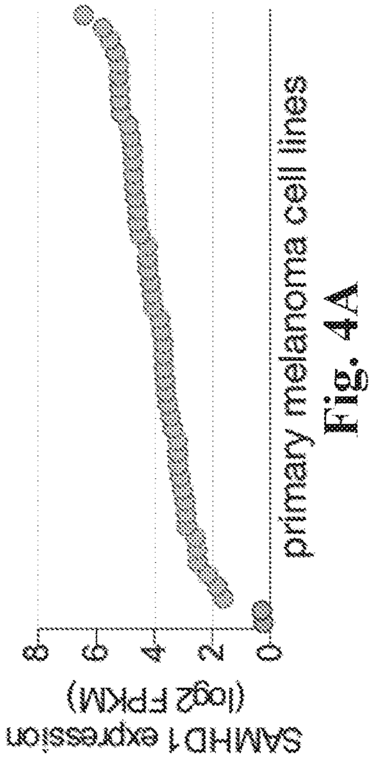
FIGS. 4A to 4D: Experimental results indicating that SAMHD1 is heterogeneously expressed in primary melanoma cell lines and SAMHD1 deficient cells are sensitive to PNP inhibition. (4A) RNAseq analysis of SAMHD1 transcript levels in a panel of 51 primary melanoma cell lines. (4B) Immunoblot analysis of representative melanoma cell lines following 24 h treatment with 100 U/mL IFNβ or 1 ng/mL IFNγ. (4C) Crystal violet staining following 7 d treatment with 1 μM PNPi (BCX-1777) in the presence of 10 μM dG. (4D) PI cell cycle analysis following 24 h treatment with 1 μM PNPi in the presence of 10 μM dG.
Figure 4B:
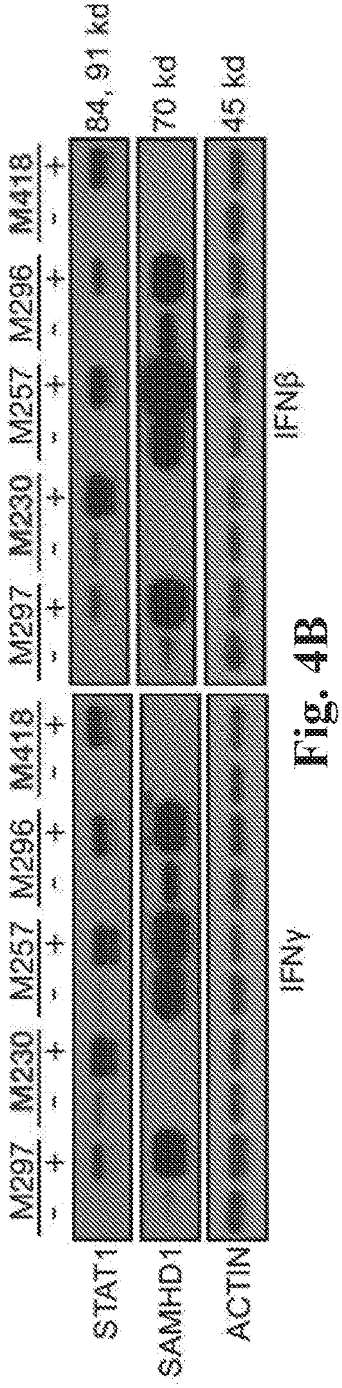

To functionally validate the role of SAMHD1 in the response of solid tumor cell line models to PNP inhibition, we generated a SAMHD1 knockout of the SAMHD1-proficient pancreatic cancer cell line SUIT2 using CRISPR/Cas9. We found that while parental cells were completely resistant to PNPi, SAMHD1 knockout cells exhibited DNA damage in response to PNPi, which could be completely prevented by supplementing with a small molecule dCK inhibitor (FIG. 3D). Additionally, using crystal violet analysis, we found that the proliferation of only SAMHD1 knockout cells could be prevented by PNP inhibitors and that this anti-proliferative effect could be completely blocked by a dCK inhibitor (FIG. 3E). Collectively, these results demonstrate that SAMHD1 expression predicts sensitivity to PNP inhibitors across leukemia and solid tumor cell line models.

a Subset of Primary Melanoma Cell Line Models are Deficient in SAMHD1 Expression and are Sensitive to PNP Inhibitors To further investigate the extent of SAMHD1-deficiency across solid tumor models, we profiled the expression of SAMHD1 in a panel of 51 primary melanoma cell lines derived at UCLA (FIG. 4A). We found that among these models, 2 exhibited undetectable levels of the SAMHD1 transcript (M230, M418). We confirmed these findings using immunoblot analysis (FIG. 4B). SAMHD1 function is tightly regulated by transcriptional, post-transcriptional and allosteric control mechanisms. In particular, SAMHD1 is an interferon-stimulated gene. Signaling initiated by type I and type II interferons (IFNs) results in up-regulation of SAMHD1 expression. To determine if SAMHD1 expression can be induced in M230 and M418 cells by IFNs, we exposed a panel of melanoma cell lines to either type I (IFNβ) or type II (IFNγ) IFN for 24 h and measured SAMHD1 expression using immunoblot analysis (FIG. 4B). We found that all models tested responded to both type I and type II interferon by increasing the expression of a canonical ISG STAT1. However, SAMHD1 expression was only increased by IFN signaling in cell line models in which SAMHD1 is detectable at baseline. The mechanism underlying impaired SAMHD1 expression in M418 and M230 cells can include mutational inactivation, which has been described in the contested of chronic lymphocytic leukemia, or aberrant promoter methylation.

Figure 4C:
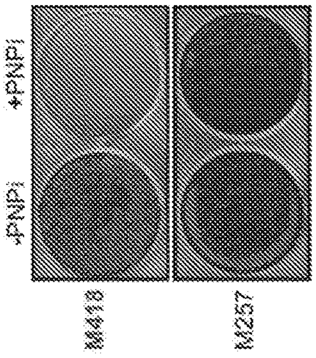
Figure 4D:
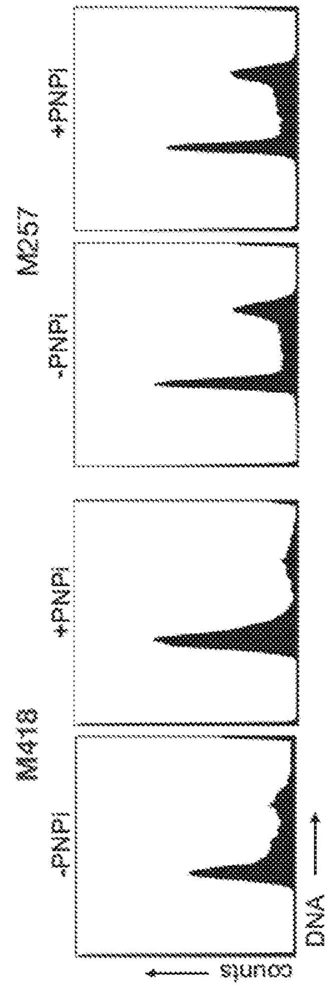

We confirmed that PNP inhibition selectively inhibited proliferation in SAMHD1-deficient primary melanoma models using crystal violet analysis (FIG. 4C). Similarly, we observed that PNPi induced cell cycle arrest only in SAMHD1-deficient models (FIG. 4D).

Deoxycytidine Mitigates the Anti-Proliferative Effects of PNP Inhibitors

Figure 5C:
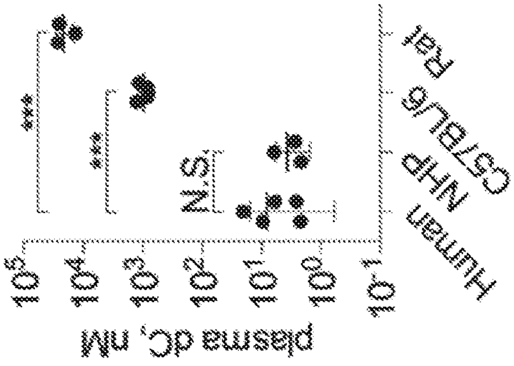
FIGS. 5A to 5C: Experimental results indicating that Deoxycytidine competes with dG for phosphorylation by dCK. (5A) Schematic overview of the competition between dC and dG for dCK. Cytidine deaminase (CDA) breaks down dC and prevents competition with dG. ENT: equilibrate nucleoside transporter. (5B) Cell Titer Glo analysis of CCRF-CEM YFP and CCRF-CEM CDA over expressing cell lines treated +10 μM dG+1 μM BCX-1777±a titration of dC for 72 h. (5C) Plasma dC in human, non-human primate (NHP), C57BL/6 and rats.
Figure 5A:
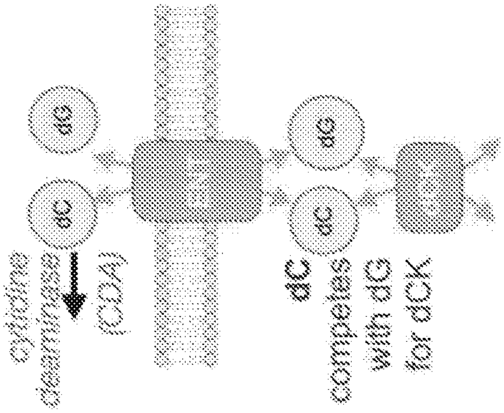
Figure 5B:
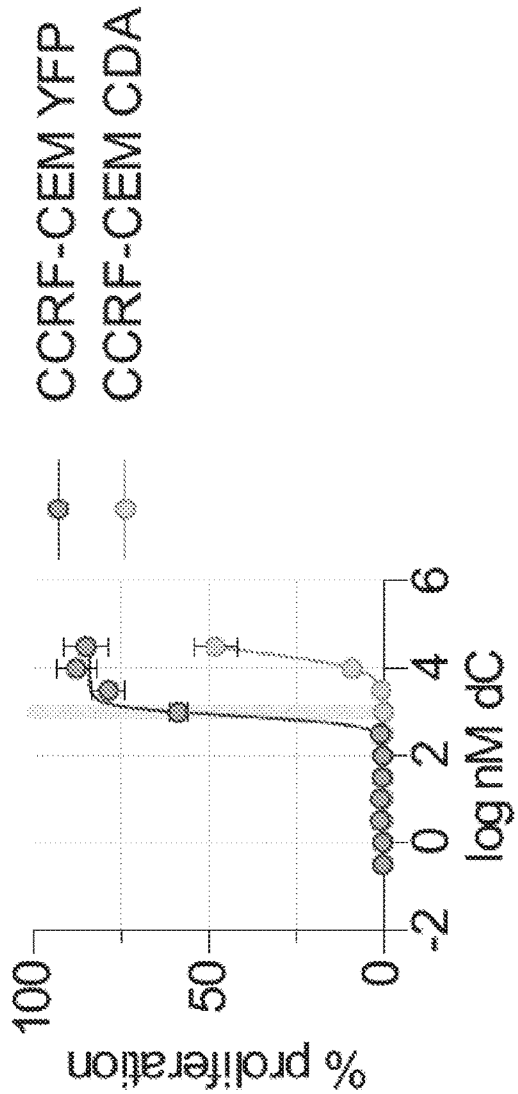

An additional factor influencing the cytotoxicity of PNP inhibitors is the competition between dG and other deoxyribonucleosides, for dCK (FIG. 5A). dCK can accept dC, dG and dA as substrates but exhibits an 15-fold higher affinity for dC over the other purine deoxyribonucleosides (BRENDA:EC2.7.1.74). Furthermore, phosphorylation of dCK by ATR further increases its ability to phosphorylate dC while not impacting dA, or dG phosphorylation. In this model, the dC catabolizing enzyme cytidine deaminase (CDA) can promote the activity of PNP inhibitors by eliminating dC and decreasing the competition at the level of dCK. To test this model, we evaluated the ability of dC to prevent the anti-proliferative effect of PNPi in CCEF-CEM YFP control cells and CDA over-expressing cells (FIG. 5B). In CCRF-CEM YFP cells, PNPi treatment decreased proliferation to 1% of control and supplementation 1 μM dC was sufficient to abrogate the effects of PNPi and restored proliferation to 60% of control. Overexpression of CDA prevented this rescue. We have previously reported that plasma deoxycytidine various greatly across species with levels ranging from 10 nM in human plasma and non-human primates to >1 μM in rodents (FIG. 5C; figure adapted from Kim et al. PNAS. 2016). It is conceivable that plasma deoxycytidine can prevent the activity of PNPi and can confound the study of PNP inhibitors in mice. Thus, high-CDA expression should be considered as another requisite biomarker for PNP inhibitors alongside low-SAMHD1 expression.

SAMHD1 Prevents the Anti Proliferative Effects of Thymidine

Figure 6A:
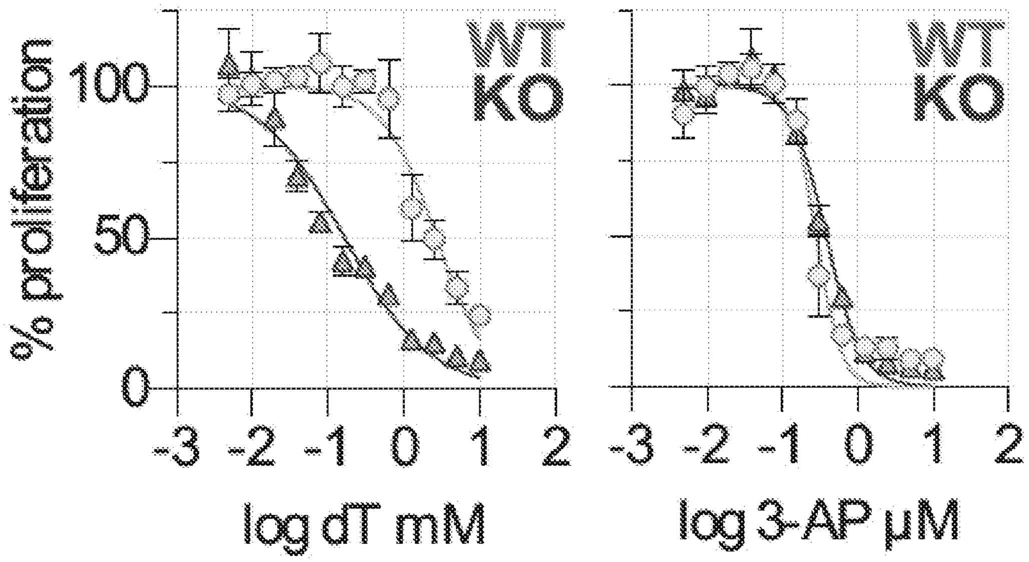
FIGS. 6A to 6C: Experimental results indicating that SAMHD1 prevents the toxicity of thymidine. (6A) Cell Titer Glo analysis of SUIT2 WT and SAMHD1 KO cells treated with a titration of dT or 3-AP for 72 h (mean±SD; n=4). (6B) Crystal violet analysis of SUIT2 WT and SAMHD1 KO cells treated for 7 d±100 μM dT. Media was refreshed every 72 h. (6C) Immunoblot analysis of SUIT2 WT and SAMHD1 KO cells treated for 24 h±100 μM dT.
Figure 6B:
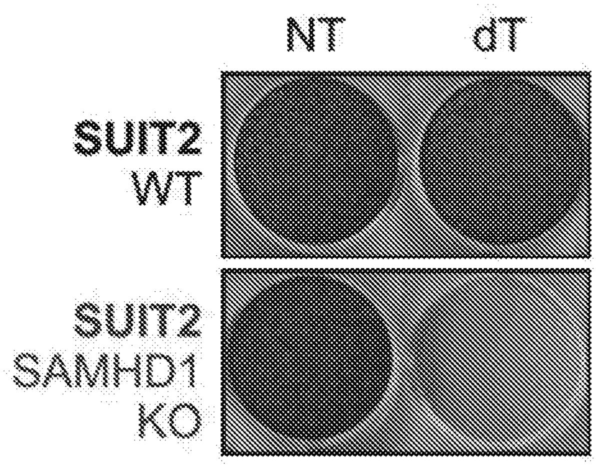
Figure 6C:
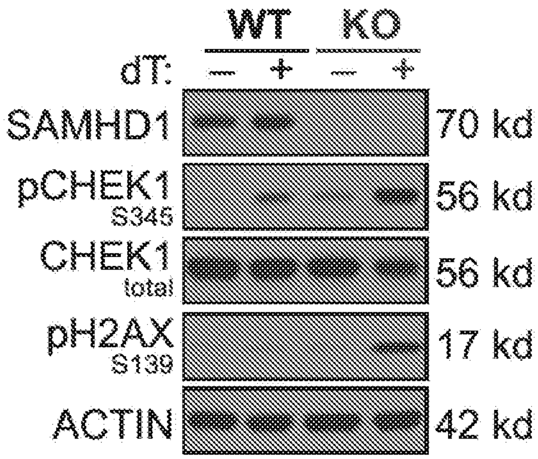

Having observed that SAMHD1 can protect cancer cells from dGTP pool imbalance resulting from PNP inhibition, we investigated whether SAMHD1 can prevent the anti-proliferative effects of imbalances in other dNTP pools. Supplementation of cell cultures with high levels of the pyrimidine nucleoside thymidine is a well-established approach to inhibit cell proliferation and arrest cells in S-phase. Additionally, this phenotype extends in vivo and is the cause of impaired T-cell development observed in dCK knockout mice. Thymidine induced cell cycle arrest is the result of allosteric inhibition of CDP reduction by ribonucleotide reductase mediated by expansion of the dTTP pool. We found that SAMHD1 KO cells exhibited a 200× lower thymidine IC-50 than SAMHD1 WT controls (FIG. 6A). This selectivity was unique to PNP inhibition and did not extend to other RNR inhibitors, including 3-AP, which function by preventing RNR tyrosyl radical regeneration. Similar selectivity was observed using crystal violet proliferation analysis (FIG. 6B). Additionally, we found that the induction of $pCHEK1_{S345}$ and $pH2A.X_{S139}$ by dT treatment was enhanced in the SAMHD1 KO cells (FIG. 6C). Collectively these results indicate that SAMHD1 protects cancer cells from toxic imbalances in both purine and pyrimidine dNTP pools.

Ulodesine and Forodesine Exhibit Similar Potency and Selectivity

Figure 7:
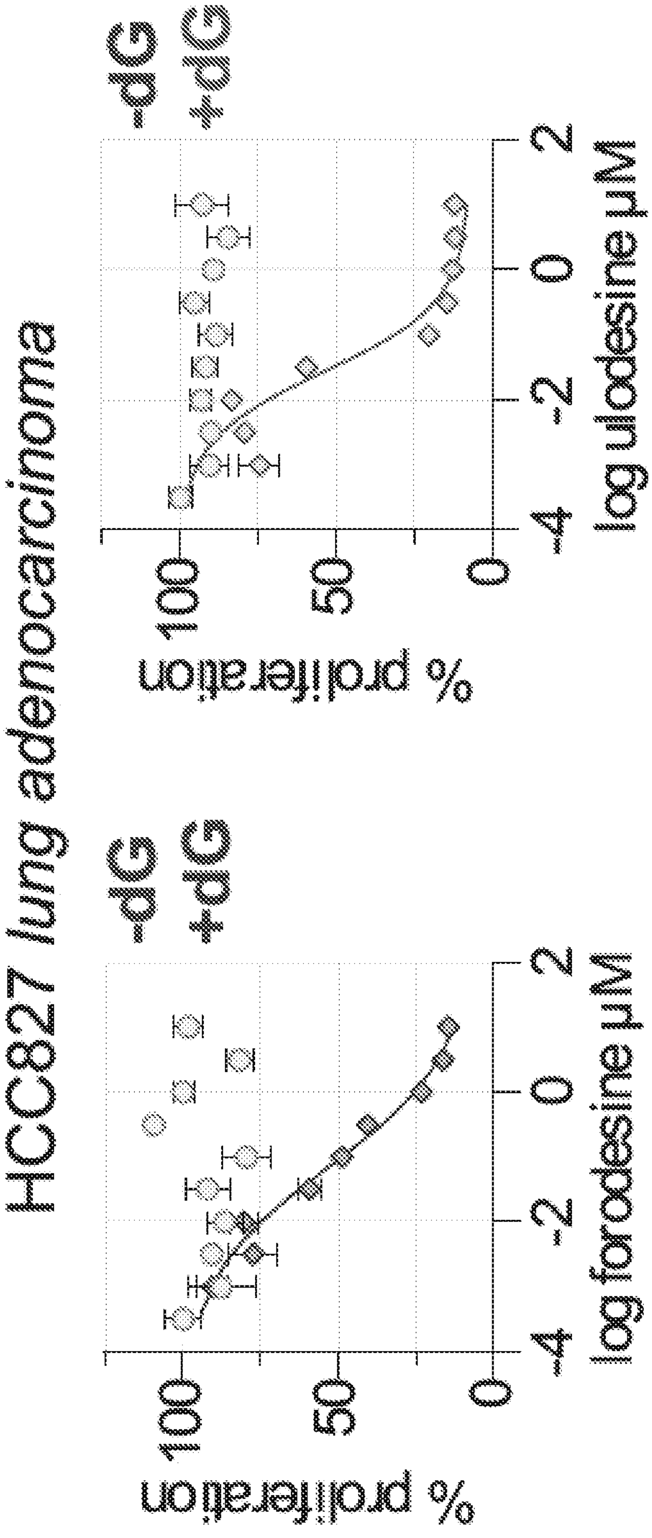
FIG. 7: Experimental results indicating that forodesine exhibits potency and selectivity similar to ulodesine. Cell Titer Glo analysis of HCC827 cells treated with a titration of forodesine (BCX-1777) or ulodesine for 72 h±10 μM dG (mean±SD; n=4).
Figure 8A:
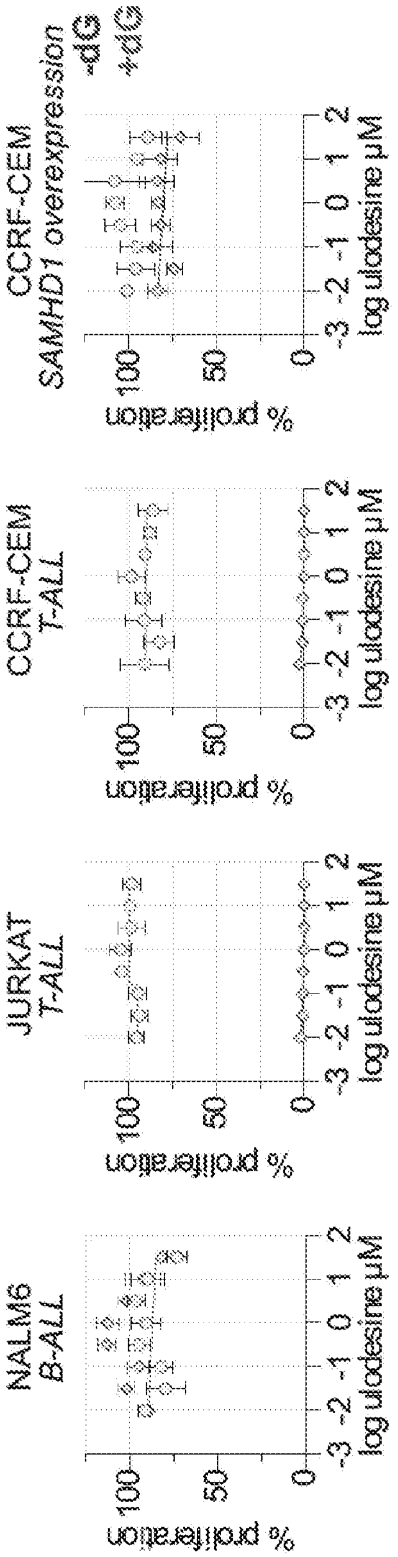
FIGS. 8A and 8B: Experimental results indicating that Ulodesine exhibits selective activity in SAMHD1-deficient cancer cell lines. (8A) Cell Titer Glo analysis of hematopoietic cancer cell lines JURKAT, NALM6, CCRF-CEM and CCRF-CEM SAMHD1 over-expressing cells treated with a titration of ulodesine for 72 h±1 μM dG (mean±SD; n=4). (8B) Cell Titer Glo analysis of solid cancer cell lines SUIT2, HCC827 and SUIT2 SAMHD1 CRISPR/Cas9 KO over-expressing cells treated with a titration of ulodesine for 72 h±5 μM dG (mean±SD; n=4).
Figure 8B:
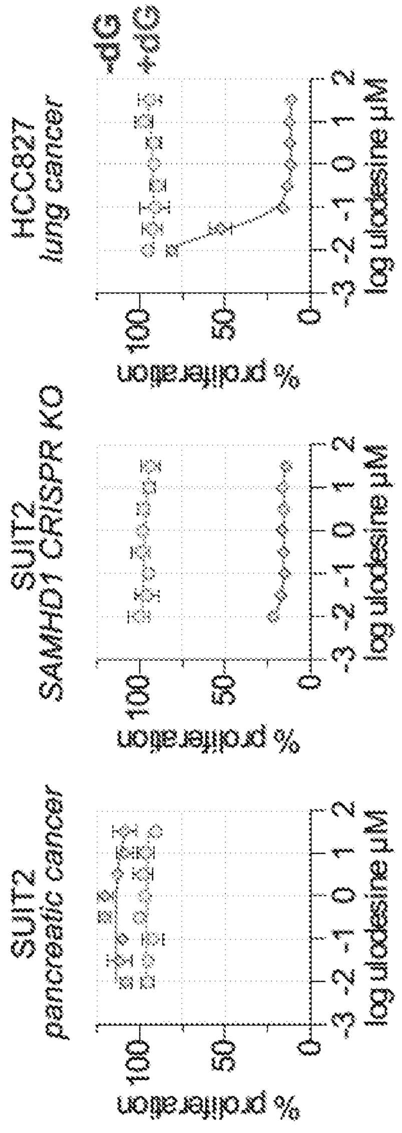

In addition to forodesine an additional small molecule inhibitor of PNP, ulodesine, has been developed in evaluated in humans for the treatment of gout. To determine if ulodesine exhibits similar potency and selectivity towards SAMHD1-deficient cancer cells we evaluated cell proliferation using Cell Titer Glo (FIG. 7). We found that both forodesine and ulodesine impaired HCC827 proliferation selectively in the presence of dG with IC50 values of 71 and 21 nM respectively. We expanded this analysis to a panel of cancer cells and found that ulodesine selectively impaired the proliferation of SAMHD1 deficient cancer cell lines JURKAT, CCRF-CEM, and HCC827 while not exhibiting any activity against towards SAMHD1-proficient SUIT2 and NALM6 cells (FIG. 8). We confirmed a role for SAMHD1 by demonstrating that overexpression of SAMHD1 in CCRF-CEM resulted in resistance, and CRISPR/Cas9 knockout of SAMHD1 in SUIT2 cells rendered them sensitive to ulodesine (FIG. 8).

REFERENCES FOR THE EXAMPLE

1. Kumar, D., Viberg, J., Nilsson, A. K. & Chabes, A. Highly mutagenic and severely imbalanced dNTP pools can escape detection by the S-phase checkpoint. *Nucleic Acids Res* 38, 3975-3983 (2010).
2. Pai, C. C. & Kearsey, S. E. A Critical Balance: dNTPs and the Maintenance of Genome Stability. *Genes* (*Basel*) 8, (2017).
3. Giblett, E. R., Ammann, A. J., Wara, D. W., Sandman, R. & Diamond, L. K. Nucleoside-phosphorylase deficiency in a child with severely defective T-cell immunity and normal B-cell immunity. *Lancet* 1, 1010-1013 (1975).
4. Kicska, G. A. et al. Immucillin H, a powerful transition-state analog inhibitor of purine nucleoside phosphorylase, selectively inhibits human T lymphocytes. *Proc Natl Acad Sci USA* 98, 4593-4598 (2001).
5. Jordan, A. & Reichard, P. Ribonucleotide reductases. *Annu Rev Biochem* 67, 71-98 (1998).
6. Shewach, D. S., Chem, J. W., Pillote, K. E., Townsend, L. B. & Daddona, P. E. Potentiation of 2'-deoxyguanosine cytotoxicity by a novel inhibitor of purine nucleoside phosphorylase, 8-amino-9-benzylguanine. *Cancer Res* 46, 519-523 (1986).
7. Kazmers, I. S. et al. Inhibition of purine nucleoside phosphorylase by 8-aminoguanosine: selective toxicity for T lymphoblasts. *Science* 214, 1137-1139 (1981).
8. Miles, R. W., Tyler, P. C., Furneaux, R. H., Bagdassarian, C. K. & Schramm, V. L. One-third-the-sites transition-state inhibitors for purine nucleoside phosphorylase. *Biochemistry* 37, 8615-8621 (1998).
9. Makita, S., Maeshima, A. M., Maruyama, D., Izutsu, K. & Tobinai, K. Forodesine in the treatment of relapsed/refractory peripheral T-cell lymphoma: an evidence-based review. *Onco Targets Ther* 11, 2287-2293 (2018).
10. Maruyama, D. et al. Multicenter phase 1/2 study of forodesine in patients with relapsed peripheral T cell lymphoma. *Ann Hematol* 98, 131-142 (2019).
11. Alonso, R. et al. Forodesine has high antitumor activity in chronic lymphocytic leukemia and activates p53-independent mitochondrial apoptosis by induction of p73 and BIM. *Blood* 114, 1563-1575 (2009).
12. Huang, M. et al. Determinants of sensitivity of human T-cell leukemia CCRF-CEM cells to immucillin-H. *Leuk Res* 32, 1268-1278 (2008).
13. Lee, J. T., Campbell, D. O., Satyamurthy, N., Czernin, J. & Radu, C. G. Stratification of nucleoside analog chemotherapy using 1-(2'-deoxy-2'-18F-fluoro-β-D-arabinofuranosyl)cytosine and 1-(2'-deoxy-2'-18F-fluoro-β-L-arabinofuranosyl)-5-methylcytosine PET. *J Nucl Med* 53, 275-280 (2012).

INCORPORATION BY REFERENCE

Each publication and patent mentioned herein is hereby incorporated by reference in its entirety. In case of conflict, the present specification, including any definitions herein, will control.

EQUIVALENTS

While specific embodiments of the subject invention have been discussed, the above specification is illustrative and not restrictive. Many variations of the invention will become apparent to those skilled in the art upon review of the preceding description and the following claims. The full scope of the invention should be determined by reference to the claims, along with their full scope of equivalents, and by reference to the rest of the specification, along with such variations.

What is claimed is:

1. A method of treating cancer comprising selecting a subject identified as having:

i) deoxynucleoside triphosphate triphosphohydrolase SAMHD1 levels that are lower than a first control level; and ii) cytidine deaminase levels that are higher than a second control level; and administering to the subject a first dose of an inhibitor of purine nucleoside phosphorylase;

wherein the inhibitor of purine nucleoside phosphorylase is forodesine or ulodesine.

2. The method of claim 1, wherein the first and second control levels are determined from a control subject or control sample that is responsive to treatment with an inhibitor of purine nucleoside phosphorylase.

3. The method of claim 1, further comprising determining test levels for deoxynucleoside triphosphate triphosphohydrolase SAMHD1 and cytidine deaminase after administering to the subject the first dose of the inhibitor of purine nucleoside phosphorylase; and administering an additional dose of the inhibitor of purine nucleoside phosphorylase if the test levels of deoxynucleoside triphosphate triphosphohydrolase SAMHD1 are lower than that of the first control level and the test levels of cytidine deaminase are higher than that of the second control level.

4. The method of claim 3, wherein the test levels for deoxynucleoside triphosphate triphosphohydrolase SAMHD1 and cytidine deaminase are determined via immunoblot analysis, RNAseq analysis, DNA sequencing, qPCR, HPLC, mass spectrometry, or a combination thereof.

5. The method of claim 1, further comprising determining test levels for deoxynucleoside triphosphate triphosphohydrolase SAMHD1 and cytidine deaminase after administering to the subject the first dose of the inhibitor of purine nucleoside phosphorylase; and administering a second dose of the inhibitor of purine nucleoside phosphorylase if the test levels of deoxynucleoside triphosphate triphosphohydrolase SAMHD1 fail to be lower than that of the first control level or the test levels of cytidine deaminase fail to be higher than that of the second control level, wherein the second dose is higher than the first dose.

6. The method of claim 1, wherein the cancer is a leukemia, a lymphoma, a melanoma, or an adenocarcinoma.

7. The method of claim 6, wherein the cancer is a leukemia, a melanoma, or an adenocarcinoma.

8. The method of claim 1, wherein the inhibitor of purine nucleoside phosphorylase is forodesine.

9. The method of claim 1, wherein the inhibitor of purine nucleoside phosphorylase is ulodesine.

* * * * *